United States Patent [19]

Gough

[11] Patent Number: 4,484,987
[45] Date of Patent: Nov. 27, 1984

[54] METHOD AND MEMBRANE APPLICABLE TO IMPLANTABLE SENSOR

[75] Inventor: David A. Gough, Cardiff by the Sea, Calif.

[73] Assignee: The Regents of the University of California, Berkeley, Calif.

[21] Appl. No.: 495,988

[22] Filed: May 19, 1983

[51] Int. Cl.³ .......................................... G01N 27/54
[52] U.S. Cl. ................................ 204/1 T; 204/403; 204/418; 435/817
[58] Field of Search ............... 204/296, 403, 415, 418, 204/1 T, 1 E; 128/635; 435/817

[56] References Cited

U.S. PATENT DOCUMENTS 3,847,777  11/1974  Haddad et al. ............... 204/415
4,073,713  2/1978   Newman ...................... 204/403
4,240,438  12/1980  Updike et al. ............. 204/403 X
4,307,195  12/1981  Karasawa et al. .......... 204/1 E X
4,317,879  3/1982   Busby et al. ................ 204/403 X
4,356,074  10/1982  Johnson ...................... 204/1 E X

OTHER PUBLICATIONS

"A Membrane Combination for Implantable Glucose Sensors, Measurements in Undiluted Biological Fluids", by Fischer and Abel, vol. XXVIII, Trans. Am. Soc. Artif., Intern. Organs, 1982, pp. 245 to 248.

Primary Examiner—G. L. Kaplan
Assistant Examiner—Nam X. Nguyen
Attorney, Agent, or Firm—Brown, Martin & Haller

[57] ABSTRACT

This invention relates to a novel membrane useful in an electro-chemical, optical or other sensor device and to a method employing the membrane for determining the concentration of large molecule compound such as glucose in an aqueous solution of that compound and a dissolved small molecule substance such as oxygen.

12 Claims, 5 Drawing Figures

METHOD AND MEMBRANE APPLICABLE TO IMPLANTABLE SENSOR

BACKGROUND OF THE INVENTION

In the disease known as diabetes mellitus, the pancreas loses its ability to manufacture and secrete insulin to counter rising blood glucose concentrations, and metabolic imbalance results. Historically, the disease has been treated by insulin injection, diet, exercise and, in limited cases, oral medication. However, the treatment has been only marginally successful at best.

A proposed solution is the artificial pancreas, a bedside device having intravenous catheters for blood glucose sampling and insulin infusion, a glucose analyzer and an insulin pump controlled by algorithms that take into account information from the glucose analyzer. But there is a clear need to develop a convenient miniature version that could be implanted to provide the patient with totally automatic metabolic regulation. A suitable insulin pump component for implantation on a clinical scale has already been developed. But the glucose sensing component remains a problem.

An electrolytic glucose sensor capable of assaying glucose in complex fluids such as blood that has been removed from the body and exposed to the atmosphere is disclosed in U.S. Pat. No. 3,542,662 to Hicks et al, dated Nov. 24, 1970. In this sensor, an enzyme-containing membrane is disposed between a fluid being assayed and a first oxygen sensor electrode and a similar membrane not containing enzyme is disposed between the fluid and a second reference oxygen sensor electrode.

In this sensor, a certain portion of the oxygen diffusing through the enzyme-containing membrane is consumed by equimolar reaction with glucose catalyzed by the enzyme and is therefore unavailable for detection by the first oxygen sensor electrode. The second, reference oxygen sensor electrode in which the membrane does not include enzyme, determines the concentration of oxygen that would have been detected had not the enzyme-promoted reaction occurred. And the difference in oxygen detected by the two electrodes is relied on as proportional to the glucose concentration.

However, when efforts were made to adapt this device for use directly in the body, confusing observations resulted. The sensors were calibrated for glucose response in the atmosphere before implantation in test animals. After a period of implantation, glucose or insulin was injected intravenously to perturb the blood glucose concentration. In the cases where there was any response to glucose, the sensor-indicated concentration was much less than expected.

The departure from expected behavior has been attributed universally to unfavorable biocompatability of the implant material. That is, implants cause the development of an encapsulating sheath which, if thick and dense, may be impermeable to glucose. However, this can be minimized by the use of appropriate materials and does not adequately account for the results secured.

A key problem is that the glucose concentration in the body is normally higher than the oxygen concentration by a factor of 50 to 100 times. Since the enzyme reaction is limited by the least abundant reactant, an implanted sensor would respond to oxygen concentration rather than to glucose concentration and therefor would be ineffective to measure glucose concentration.

One proposal to solve this problem presented in an article by Fischer and Abel entitled "A Membrane Combination for Implantable Glucose Sensors, Measurements in Undiluted Biological Fluids" in Trans. Am. Soc. Artif. Intern. Organs, Vol. XXVIII, 1982, involved sandwich membranes for association with an oxygen electrode sensor. In these membranes, a hydrophobic layer was disposed to cover an enzyme layer and a minute hole directly aligned with the anode of the sensor was provided in the hydrophobic layer to allow access of glucose from blood being assayed without dilution to the enzyme and anode. Oxygen diffusing through the surface of the entire hydrophobic layer was indicated to provide a stoichiometric excess over the glucose.

The space and time within which reaction between glucose and oxygen must occur in this arrangement are so limited as to impose limits on the range of concentrations of glucose with which complete reaction can occur and could affect the reliability of results obtained. Additionally, the small amount of enzyme disposed for action on glucose entering the minute hole tends to become inactivated in a relatively short time.

BRIEF SUMMARY OF THE INVENTION

The assay method of the present invention operates to determine the concentration of a first component present in solution in stoichiometric excess over a second component reactive with the first component by diffusing the solution through a special membrane which reduces the rate at which the first component in the solution passes through the membrane to a value which is a function of the initial concentration, increases the concentration of the second component so that the second component is present in stoichiometric excess over the first component in the solution which has passed through the membrane. After reaction of the first and second component, the amount of unreacted second component or the amount of reaction product is measured to determine the concentration of the proportion of first component which has passed through the membrane.

The membrane of the present invention is a combination of a body of hydrophilic material, which contains immobilized enzymes or catalyst for promoting reaction between components from a body of an aqueous solution and which provides a path through the membrane to a detector for dissolved components from an aqueous solution of the components accessible to a surface of the membrane, and a body or bodies of hydrophobic material permeable to some but not all of the dissolved components disposed relative to the hydrophilic material to effect a controlled change in the relative proportions of the dissolved components from the proportions existing in the original solution. In the membrane, the enzymes are disposed in quantity and relation for long life and effective action on the components, and the hydrophilic and hydrophobic bodies are arranged to provide space and time for complete reaction of the components.

DRAWINGS

Reference is made to the drawings illustrating various embodiments of the invention in which.

DETAILED DISCLOSURE OF THE INVENTION

Figure 1:
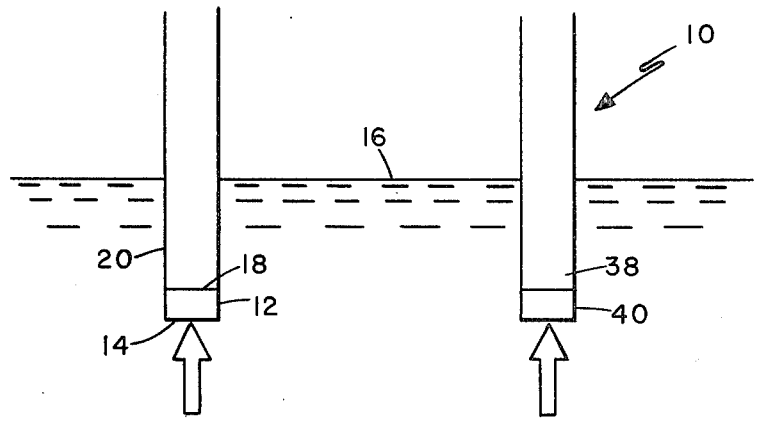
FIG. 1 is a schematic diagram of a sensor for operation according to the present and employing the membrane of the present invention.

A sensor 10 incorporating the membrane 12 of the present invention is shown (FIG. 1) with a surface 14 of the membrane 12 accessible to an aqueous body 16 containing dissolved components of which the molecules of one component are much larger or less soluble than the molecules of a second component, and with the other membrane surface 18 adjacent a detector 20 for the second component. The membrane 12 is an association of a body of hydrophilic material and a body or bodies of hydrophobic material arranged in relations, such as shown in FIGS. 2 to 5, which may restrict the rate at which the larger molecule component enters and passes through the membrane 12 and/or may increase the rate at which the second component enters and passes through the membrane.

The hydrophilic material of the membrane is permeable to both a large molecule component such as glucose and a small molecule components, such as oxygen, in the solution and is disposed to provide a path through the membrane from the body of solution being assayed.

An enzyme or a catalyst for promoting the reaction between the large and small molecule components may be immobilized in the hydrophilic material for action on these components as they diffuse through it. Or alternatively a separate enzyme-, or catalyst-containing component may be provided for action on the components that have passed the membrane.

The hydrophobic material of the membrane is impermeable to the larger or less soluble molecule component but permeable to the smaller or more soluble molecule. This hydrophobic material may be disposed in a body or bodies which limit the surface area of hydrophilic material exposed for accepting large molecule components from the solution and thus reduce the rate of entry of such components to a value which is a function of the concentration existing in the solution, so that the rate of component entering is that which would enter from a more dilute solution in the absence of the hydrophobic material. Additionally, substantial surface area of hydrophobic material is provided for accepting the small molecule component. Alternatively, the hydrophobic component may be dispersed as small domains in a continuous phase of the hydrophilic material to reduce the front along which the large molecule component can be transported and so reduce its effective diffusion coefficient or transport rate, while the small molecule material can diffuse at a high rate since it can move through both the hydrophilic material and hydrophobic domains. The result of limitation of the rate of entry and/or transport of the larger molecule component and the increased rate of entry and transport of the smaller molecule increases the ratio of small molecule material to large molecule material passing through the membrane to the detector.

In the following disclosure, the invention will be referred to primarily in the assay of glucose in solutions such as blood, containing a large stoichiometric excess of glucose over oxygen; but it is to be understood that the membrane and method of the invention are not limited to this use or assay of this material, but may be used for the assay of other large molecule compounds such as lactates, cholesterol and others in solution containing oxygen, ammonia or other low molecular components reactive with the larger molecule components. Also the sensor primarily referred to is electrolytic and includes an oxygen-sensitive electrode detector which may be similar to the oxygen-sensitive electrode detectors of the Hicks et al patent referred to above; but non-electrolytic sensors using optical, e.g. glass fiber optics, or other known detectors may be used.

A parameter used as a first approximation to show the relationship between factors affecting entry and transport of components in the membrane is $$\bar{c}_o^* = \frac{\alpha_o c_{oB} D_o}{\gamma_o \alpha_g c_{gB} D_g}$$

where $\alpha$ is the partition coefficient, $D$ is the diffusion coefficient, $c$ is the concentration, $\gamma_o$ is a stoichiometry coefficient that may range from 0.5 to 1.0, the subscripts o and g refer to oxygen and glucose respectively, and the subscript B refers to the concentration of that solute in the well-mixed bulk phase of the sample. Other factors that affect the ratio of substrates in the membrane are: the external mass transfer resistance, the enzymatic reaction, and whether or not the sensing electrode consumes the oxygen that it senses. These latter factors are important to the operation of the sensor, but are irrelevant to this discussion. When the value $\bar{c}^*_o$ of is greater than or equal to unity, there will be adequate oxygen in the membrane and the system will be glucoselimited and capable of assaying glucose. Thus, from the anticipated bulk glucose and oxygen concentrations that the sensor will be exposed to, the ratio of the parameters to maintain $\bar{c}_o^* \geq 7$ and reliably determine glucose may be determined.

The diffusion coefficient $D$ indicates how fast the respective solute can move once within the membrane. A smaller solute such as oxygen can diffuse faster in most materials than a larger molecule like glucose. In membranes, the rate of diffusion is determined by the internal microscopic structure, the degree of crosslinking of the network or "tightness", and the flexibility of the polymeric chains composing the membrane. In principle, increasing the crosslink density of a membrane should be favorable for alleviating the oxygen deficient, since this would slow the rate of glucose diffusion to a greater extent than it would affect oxygen. However, in practice, it is difficult to crosslink hydrophilic gel membranes to that extent that the differential retardation of glucose could achieve the differences needed here.

The partition coefficient $\alpha$ indicates the solubility of the solute in the membrane and is determined by the type of bonding that can exist between the solute and the membrane material. For example, a hydrophilic or "water loving" solute such as glucose is readily partitioned into a hydrophilic, gel-type material, but is excluded from a hydrophobic material. The enzymes are hydrophilic and also partition into this type of material. Oxygen dissolves to some extent in water and therefore can also partition into a hydrophilic material, but in addition is soluble in certain hydrophobic materials. Oxygen is, in fact, highly soluble and diffusible in certain hydrophobic materials such as silastic rubber. This feature is used here. Changing the membrane thickness is not advantageous since it affects both solutes to the same extent.

Figure 2:
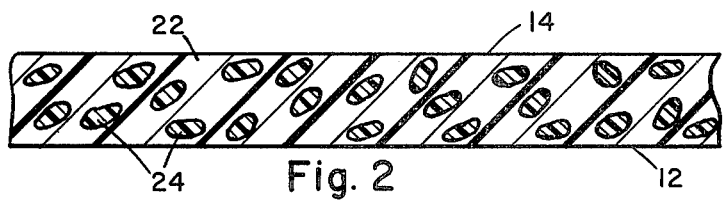
FIG. 2 is a cross-section on an enlarged scale illustrating one form of the membrane of the present invention.
Figure 3:
FIG. 3 is a cross-section on an enlarged scale illustrating a second form of the membrane of the present invention.
Figure 4:
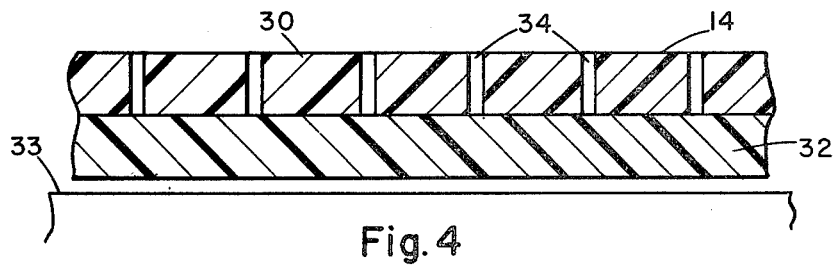
FIG. 4 is a cross-section on an enlarged scale of a further form of the membrane of the present invention.

In the membrane embodiment shown in FIG. 2, the membrane 12 is formed with a continuous phase 22 of hydrophilic material in which very small bodies or domains 24 of hydrophobic material are distributed. Hydrophilic materials useful in the continuous phase include polyacrylamide gel, glutaraldehyde-crosslinked collagen, polyhydroxyethylmethacrylate and its derivatives and other hydrophilic polymers and copolymers. A hydrophilic polymer can also be made by crosslinking oxidase or other enzymes with glutaraldehyde or other crosslinking agents.

Hydrophobic materials for association with the continuous phase 22 of hydrophilic material include polydimethylsiloxane, polymers of tetrafluoroethylene or its fluoro-chloro analogues alone or as copolymers with ethylene or propylene, polyethylene, polypropylene, cellulose acetate and other oxygen-imbibing polymeric materials. These materials will be included in amount of from about 2% to about 40% of the weight of the membrane.

A number of procedures are available for combination of the hydrophobic material with the hydrophilic material. The hydrophobic material in solid form may be fractured or milled into micron particle size, in the range of from about 1 to about 10 microns, treated with a surfactant such as gamma-aminopropyltriethoxysilane and mixed with fluid uncrosslinked or unreacted, e.g. monomeric or partially polymerized hydrophilic phase material preferably containing enzyme or catalyst material. The mixture is subsequently cast as a thin layer and crosslinked or polymerized to solidify it. Or the hydrophobic material may be in the form of a latex of which the small particles of hydrophobic material already carry surfactant and are suspended in water so that the material is readily mixed with the fluid hydrophilic material.

In another procedure, a viscous polymeric hydrophobic material is mixed with or entrapped in the hydrophilic material. For example, viscous polydimethylsiloxane of various molecular weights have been mixed with collagen or with polyacrylamide and cast as a membrane.

In an alternative arrangement (see FIG. 3), the hydrophobic material is a highly porous film or solid 26 which is treated with a surfactant, filled with fluid hydrophilic material 28 and treated to crosslink or polymerize the hydrophilic material in place to form an interpenetrating network structure.

Another form of membrane (see FIG. 4) disposes the hydrophobic material as a stratum 30 covering a hydrophilic stratum 32 and formed with spaced small openings 34, having a size and number to control the entry of the large molecule substrate into the hydrophilic stratum 32 while providing a broad surface for entry of the gas. In this form, glucose entering the openings 34 diffuses through the stratum 32 between the hydrophobic stratum 30 and the surface of the detector 33 generally parallel to the face of the membrane toward the electrode 35 and reacts with oxygen entering through the hydrophobic stratum 30 through the action of enzyme or catalyst present in the stratum 32.

A further form of the membrane (see FIG. 5) disposes the hydrophilic component as a thin, preferably immobilized enzyme-containing a layer 36 with a thin layer 38 of hydrophobic component covering a portion or all of the face 40 of the hydrophilic layer 36 leaving the edge surfaces 42 due to the thickness of that layer accessible to the solution.

Figure 5:
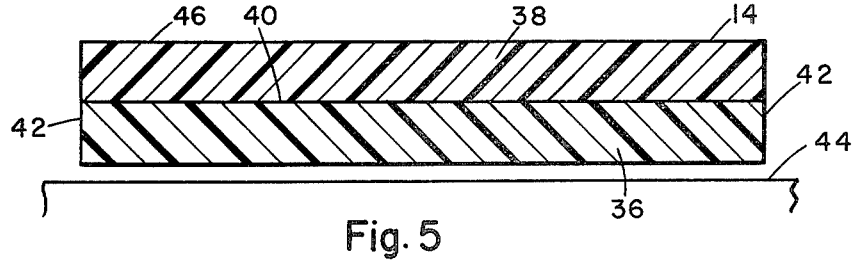
FIG. 5 is a cross-section on an enlarged scale of a still further form of the membrane of the present invention.

In the membrane shown in FIG. 5, the large molecule material, such as glucose, enters the membrane only through the edge surfaces 42 of the hydrophilic layer 36 and diffuses toward the center portion substantially parallel to the face of the membrane between the hydrophobic layer 38 and the surface of the detector element 44 which may be an oxygen electrode. The reactive gas, e.g. oxygen, can enter the membrane through the entire exposed surface 46 of the hydrophobic layer 38 and insures that there is an excess of oxygen over glucose.

This last form of membrane offers special advantages in enabling longer enzyme activity. In the previous forms, there is need to make the membrane as thin as possible and as the enzyme becomes inactive, the substrates can effectively diffuse farther and farther into the membrane before encountering active enzyme. Ultimately the substrates can diffuse all the way across the membrane without reaction and a sensor would no longer detect glucose.

But with the design of FIG. 5, advance of inactivation is effectively in the direction of glucose diffusion parallel to the plane of the oxygen electrode. The dimension in this direction can be made very long, thus allowing a great reserve.

The configuration of this form can be made in a variety of geometries in addition to the one shown in FIG. 5. Thus, the oxygen electrode could be made as a cylinder with a circumferential hydrophilic coating containing enzymes and with a hydrophobic coating over the side of the hydrophilic coating. In this configuration, glucose could enter only through the hydrophilic exposed edge and oxygen could enter through the sides.

Still another arrangement is a combination of a circular plate oxygen electrode with an enzyme-containing layer on each side and with a hydrophobic layer on the outer side of this layer. This allows oxygen to enter from both directions perpendicular to the plate and glucose to enter from the circumferential edges.

In operation of an electrode sensor 10 (see FIG. 1) for determining the concentration of glucose in a body 16 of a solution containing dissolved glucose and oxygen using a membrane 12 containing immobilized glucose oxidase and catalase, the oxidase enzyme promotes the following reaction:

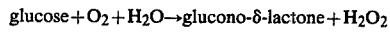

and the lactone hydrolyzes spontaneously to gluconic acid. The $H_2O_2$ may be decomposed by the catalase in the reaction:

A certain portion of the oxygen diffusing through the membrane 12 is consumed by equimolar reaction with glucose catalyzed by the enzyme and therefor unavailable for detection by the oxygen sensor electrode 20. An identical reference oxygen sensor electrode 38, employing a similar membrane 40 which does not contain enzyme, determines the concentration of oxygen that would have been detected had no enzyme reaction occurred. With the appropriate sensor design, the difference in oxygen detected will be proportional to the glucose concentration.

However, for the system to provide useful results, the glucose concentration, as opposed to oxygen concentration, must be the limiting factor. Since the reaction is limited stoichiometrically by whichever component is present at the oxygen sensitive electrode in lowest concentration, in order to make the system sensitive to glucose concentration, oxygen must be present at the electrode in excess of the glucose.

In the relation encountered in an implanted sensor, the normal concentration of glucose in the blood, and presumably in the interstitial fluid, is approximately 100 mg % or $5.5 \times 10^{-3}$M but may be much higher on diabetics, while that of oxygen is likely to be 40 mm. Hg, or only about $6 \times 10^{-5}$M.

In operation of the present sensor, according to the method of the present invention, to insure response to glucose at tissue pO$_2$, the enzyme membrane 12 is designed so that oxygen passes readily into and through the membrane and that a reduced amount of glucose, which is a function of the concentration of glucose in the solution, diffuses into and through the membrane 12 for reaction with the oxygen. The ratio of oxygen to glucose is controlled by the entry and/or transport properties of the special membrane so that the relative proportions are changed from a concentration ratio in the body of liquid, e.g. blood, of between approximately 50 and 100 parts of glucose to one of oxygen to a new ratio in which a slight stoichiometric excess of oxygen exists in the membrane. By this action, the system is not stoichiometrically limited by the concentration of oxygen in the body fluid and the system can operate on the simplifying assumption that the reaction behaves as a one-substrate (glucose) dependent process.

The following examples are given to aid in understanding the invention, but it is to be understood that the invention is not limited to the particular materials or procedures of the examples.

EXAMPLE 1

Five grams of bovine collagen is suspended in 40 ml. of pH 7 aqueous phosphate buffer and the suspension is heated in an autoclave at 100° C. After removal from the autoclave and cooling, a clear viscous liquid was obtained.

A polytetrafluoroethylene latex (Teflon latex from DuPont) having a particular size of 1 to 5 microns and a solids content of 10% was added in proportions of 6.6 ml. of the latex to 3.3 ml. of the autoclave collagen product, and 0.4 g. of glucose oxidase enzyme was added to the above mixture and uniformly distributed therein.

The resultant mixture was cast on a glass surface as a layer of 10 mils wet thickness and allowed to dry at room temperature for five hours. The dried product was a film 3 mil in thickness. A 50% aqueous glutaraldehyde was poured directly on the film and distributed uniformly over the surface. The film was then rinsed to remove free glutaraldehyde and peeled from the glass surface.

A disk 1 cm. in diameter was cut from the film and edge bonded with cyanoacrylate adhesive to the detector end of an electrolytic oxygen sensor. The sensor was placed in a sealed vessel at known physiologic oxygen concentration with the detector end immersed in physiologic buffer solution; and the current due to the oxygen in the vessel was measured at 10 microamps.

Aliquots of glucose solution were added to the buffer solution in the vessel in amounts to raise the glucose concentration by 1 mM for each addition. The current due to glucose dependent oxygen was measured after each addition and this was compared with the current generated by the original buffer solution before glucose was added. The following table lists the difference between these two currents after each aliquot addition.

|  | ALIQUOT ADDITIONS | | | | | |
| --- | --- | --- | --- | --- | --- | --- |
|  | 0 | 1 | 2 | 3 | 4 | 5 |
| Microamps With Teflon | 0 | 2 | 4 | 6 | 8 | 10 |
| Microamps Without Teflon | 0 | 4 | 8 | 10 | 10 | 10 |

EXAMPLE 2

A membrane is prepared as in Example 1, except that 0.4 g. of l-lactate oxidase obtained from *M. phlei* is immobilized in the mixture rather than glucose oxidase.

A disc 1 cm. in diameter is cut from the film and edge bonded with cyanoacrylate adhesive to the detector end of an electrolytic oxygen sensor. The sensor is placed in a sealed vessel at known physiologic oxygen concentration with the detector end immersed in physiologic buffer solution. The current due to the oxygen in the vessel is measured at 10 microamps.

Aliquots of l-lactic acid are added to the buffered solution in amount to raise the l-lactic acid concentration by 1 mM for each addition.

The current due to lactic acid dependent oxygen is measured after each addition and is compared with the current generated in the original buffer solution before addition of the lactic acid. The results are similar to the results which were obtained in Example 1.

I claim:

1. A membrane for disposition with a surface accessible to a body of an aqueous solution of a gas and a stoichiometric excess of a compound reactive with said gas to provide a path between said body and a detector, said membrane comprising hydrophilic material permeable to said gas and to said compound for transport to said detector, immobilized enzyme or catalyst disposed for contact with said gas and said compound along said path for promoting reaction between said compound and said gas and small domains of hydrophobic material permeable to said gas and impermeable to said compound distributed in intimate contact with a continuous phase of said hydrophilic material, said domains being present in quantity, size and arrangement to provide good permeability of the membrane to said gas, to supply said gas to said compound diffusing along said path, to restrict the rate at which said compound enters and/or is transported through said membrane to a value which is a function of the initial concentration of said compound in said solution and is reduced relative to the rate of entry and/or transport of said gas to provide a new concentration ratio of said gas to said compound passing said membrane at least equal to a stoichiometric equivalent and to provide in the path, space and time for substantially complete reaction of said gas and the said compound at the restricted rate of entry and/or transport of said compound in said membrane.

2. A membrane as defined in claim 1 in which said enzyme or catalyst is immobilized in said hydrophilic material for promoting reaction between said compound and said gas.

3. A membrane as defined in claim 1 in which said hydrophobic material is at least one member selected from the group consisting of polydimethylsiloxane, polymers of tetrafluoroethylene or its fluoro-chloro analogues alone or as copolymers with ethylene or propylene, polyethylene, polypropylene, cellulose acetate and other oxygen-imbibing polymeric materials.

4. A membrane as defined in claim 1 in which said hydrophilic material is at least one member selected from the group consisting of polyacrylamide gel, glutaraldehyde-crosslinked collagen, polyhydroxyethylmethacrylate and its derivatives and other hydrophilic polymers and copolymers.

5. The method for determining the concentration of a first component present in stoichiometric excess over a reactive gas component in an aqueous solution, said method comprising the steps of diffusing said components through a membrane providing a continuous path of hydrophilic material for entry and transport of both of said components from a membrane surface accessible to a body of said solution to a detector, contacting said first component and said gas with immobilized catalyst along said path for promoting reaction between said first component and said gas, supplying said gas to said first component diffusing along said path through small domains of hydrophobic material permeable to said gas and substantially impermeable to said first component disposed in a continuous phase of said hydrophilic material along said path in quantity, size and arrangement to provide good permeability of the membrane to said gas and to restrict the rate at which said first component enters and/or is transported through said membrane to a value which is a function of the initial concentration of said first component in said solution and which is reduced relative to the rate of entry and/or transport of said gas component to provide a new ratio of said gas component to said first component passing said membrane at least equal to a stoichiometric equivalent, substantially completely reacting said first component entering said membrane with said gas in the space and time of movement through said membrane and measuring the concentration of any unreacted gas or of the reaction product of said gas and said first component.

6. A method as defined in claim 5 in which said enzyme or catalyst is immobilized in said hydrophilic material.

7. A method as defined in claim 5 in which said first component is an oxidizable compound and said gas component is oxygen.

8. A method as defined in claim 7 in which said oxidizable compound is glucose and said membrane contains immobilized oxidase.

9. A method as defined in claim 8 in which said hydrophilic material provides a conductive path through said membrane to an oxygen detector.

10. A method as defined in claim 7 in which said oxidizable compound is lactic acid and said membrane contains immobilized 1-lactate oxidase.

11. A method as defined in claim 5 in which said hydrophobic material is at least one member selected from the group consisting of polydimethylsiloxane, polymers of tetrafluoroethylene or its propylene, polyethylene, polypropylene and cellulose acetate.

12. A method as defined in claim 5 in which said hydrophilic material is at least one member selected from the group consisting of polyacrylamide gel, glutaraldehyde-crosslinked collagen and polyhydroxyethylmethacrylate and its derivatives.

* * * * *